US00PP09132P

United States Patent [19]

Moser

[11] Patent Number: Plant 9,132

[45] Date of Patent: May 9, 1995

[54] AZALEA PLANT NAMED YB 871 REMEMBRANCE

[75] Inventor: Frank C. Moser, Alva, Fla.

[73] Assignee: Yoder Brothers, Inc., Barberton, Ohio

[21] Appl. No.: 223,996

[22] Filed: Apr. 6, 1994

[51] Int. Cl.[6] ..... A01H 5/00

[52] U.S. Cl. ..... Plt./57

[58] Field of Search ..... Plt. 55, 56, 57

[56] References Cited

PUBLICATIONS

Lee, F. P., "Evergreen Species and Named Varieties" *The Azalea Book* 2nd Ed., D. Van Nostrand Co., Ind., N.J. 1965, p. 343.

*Primary Examiner*—James R. Feyrer
*Attorney, Agent, or Firm*—Foley & Lardner

[57] ABSTRACT

An azalea plant named YB 871 Remembrance, particularly characterized by its evergreen foliage, semi-double flower form, dark pink flower color, ease of forming flower buds, free branching, uniform plant habit and flowering response in a year round controlled program, excellent cooler tolerance, and its keeping quality.

1 Drawing Sheet

1

The present invention comprises a new and distinct cultivar of Azalea, a greenhouse forcing type, hereinafter referred to as YB 871 Remembrance.

YB 871 Remembrance, identified as Code 871 during the selection process, originated from a planned cross hybridization between two selected breeding lines in a controlled breeding program in Fort Myers. Fla. by the inventor Frank C. Moser.

The female, or seed parent of YB 871 Remembrance is the commercial cultivar Prize, a dark rose pink double hose-in-hose with vigorous upright habit and disclosed in U.S. Plant Pat. No. 3,795. The male, or pollen parent is a seedling known as Code 227, a proprietary breeding line.

YB 871 Remembrance was discovered and selected as one flowering plant within the progeny of the stated cross by the inventor Frank C. Moser in October 1988, in Fort Myers, Fla.

The first asexual reproduction of YB 871 Remembrance was accomplished when vegetative cuttings were taken from the initial selection in December, 1988, in Fort Myers, Fla., by technicians working under formulations established and supervised by Frank C. Moser.

Horticultural examination of controlled flowerings of successive generations of plants derived from cuttings taken from the original selection has shown that the unique combination of characteristics as herein disclosed for YB 871 Remembrance are fixed and retained through successive generations of asexual reproduction.

YB 871 Remembrance has not been observed under all possible environmental conditions. The phenotype may vary significantly with variations in environment such as temperature, light intensity and day length, without, however, any variance in the genotype.

The following observations, measurements and comparisons describe plants that were grown in Fort Myers, Fla., in a controlled greenhouse environment and following a commercial schedule.

The following traits have been repeatedly observed and are determined to be basic characteristics of YB 871 Remembrance, which in combination distinguish this azalea as a new and distinct cultivar:

2

1. A bright dark pink flower color (57C) upon opening, fading to a lighter pink color (68B) as flowers age.
2. Semi-double to single flowers which range in size from 6.5 to 9.0 cm in diameter with 7.5 cm the average size.
3. Compact, uniform symmetrical, free branching plant habit.
4. Rapid uniform response in year round controlled flowering programs, forcing in 26 days on average.
5. Long lasting flowers, with flowers in a simulated home environment lasting up to 18 days.
6. Dark green glossy evergreen foliage.
7. Excellent foliage retention and no flower bud damage when cooled for 6 weeks with no lighting at 38° F.

The accompanying color photograph shows in perspective view the unique features of the new cultivar, with colors being as true as possible with color illustrations of this type.

Of the commercial cultivars known to the inventor, the most similar in comparison to YB 871 Remembrance is Solitaire, disclosed in U.S. Plant Pat. No. 3,171. YB 871 Remembrance is somewhat similar to Solitaire in pink flower color, flower size and rapid flower response.

YB 871 Remembrance differs from Solitaire in that Solitaire has a hose-in-hose flower form whereas YB 871 Remembrance does not. The plant habit of YB 871 Remembrance is more dense and uniform than that of Solitaire. The foliage of Remembrance is smaller, darker green and glossier than the foliage of Solitaire.

In the following description color references are made to the Royal Horticultural Society Colour Chart. The color values were determined on Feb. 7, 1994. All readings were taken in an office under cool white fluorescent lights, facing a west window between the hours of 10:00 a.m. and 2:00 p.m.

Classification:

*Botanical.*—Rhododendron hybrida, evergreen type.

*Commercial.*—Florist forcing pot azalea.

INFLORESCENCE

A. Flower (General):

*Size.*—6.5 to 9.0 cm in diameter.

*Born.*—Terminal cluster, usually 3 per bud, ranging from 2–4. Usually one bud per stem.

*Form.*—Semi-double to single. Funnel-form.

*Blooming habit.*—Once, profusely. Buds easily and uniformly in a year round flowering program. The majority of terminal buds break color within one week of the first. Flowering begins approximately 26 days after the start of forcing.

*Fragrance.*—None.

B. Corolla (Petals):

*Texture.*—Soft.

*Substance.*—Heavy.

*Shape.*—Rounded and smooth.

*Color (fully open).*—Generally 57C, dark pink, fading to 68B as flowers age. Upper surface: Edge: 57C. Center: 57C to 57D. Base: 62A, occasionally very short staminodes present which are white (closest to 155D but lighter in color). Lower surface: 57D. Blotch: 57B.

C. Bud:

*Size.*—Medium.

*Shape.*—Conoidal.

*Color.*—61C.

*Bud sheath.*—Light green with light brown hairs.

D. Calyx:

*Form.*—Acute.

*Color.*—145B Yellow-green group.

E. Peduncle:

*Length.*—0.7–1.4 cm.

*Strength.*—Strong.

*Aspect.*—Pubescent.

F. Reproductive organs:

*Androecium (stamens).*—Number: Usually 5, sometimes six. Some are partially transformed into petals. Anthers: 61B. Filaments: Length: 1.5 to 3.5 cm. Color: 61D.

*Gynoecium (pistil).*—Stigma: 61A. Style: Length: 2.5–4.5 cm. Color: 61D. Ovary: Pubescent.

PLANT CHARACTERISTICS

A. Foliage:

*Type.*—Evergreen.

*Arrangement.*—Alternate.

*Shape.*—Elliptic, apex mucronate to acute.

*Size.*—Length: 2.6–6.0 cm. Width: 0.8–2.4 cm.

*Margin.*—Entire.

*Color.*—Immature: Upper surface: 143A. Lower surface: 143C. Mature: Upper surface: 139A. Lower surface: 137C.

*Texture.*—Leathery.

*Tomentum.*—Present on upper surface. Insignificant.

B. Stems:

*Color.*—Immature: 145B. Mature: 165A. Tomentum: 165A.

C. Plant habit: Compact, semi-upright bush which achieves a uniform, symmetrical plant in a six inch pot when pinched three times. Total crop time to the dormant budded stage is 40–42 weeks to produce a plant approximately 26–34 cm in diameter and a total height of 24–32 cm. Internode lengths vary widely from 2 to 15 mm on the same stem.

D. Branching habit: Free branching, producing 4 to 5 breaks when a vegetative cutting is pinched.

E. Rooting: Roots easily in 8 to 10 weeks with 75° F. soil temperature.

F. Budding ease: Plants produce flower buds easily and uniformly year round with the use of commercially available plant growth regulators. Natural season response has not been ascertained.

H. Cooler tolerance: Plants placed in a cooler as a means of breaking dormancy perform very well. YB 871 Remembrance is tolerant of six weeks in an unlighted cooler at 38° F. without foliage loss or bud damage.

I. Blooming: Plants reach the stage of 12 buds showing color in 26 days on average after the cooling treatment. This varies from 12 to 38 days depending upon temperature and stage of flower bud development at the start of forcing. YB 871 Remembrance flowers uniformly and profusely across the plant and down the sides.

J. Shelf-life: When plants are moved to an office or home environment at the stage of eight open flowers, they maintain an attractive appearance for 18 days on average. Flowers are not persistent, falling off once flowers senesce.

I claim:

1. A new and distinct cultivar of azalea named YB 871 Remembrance, as described and illustrated.

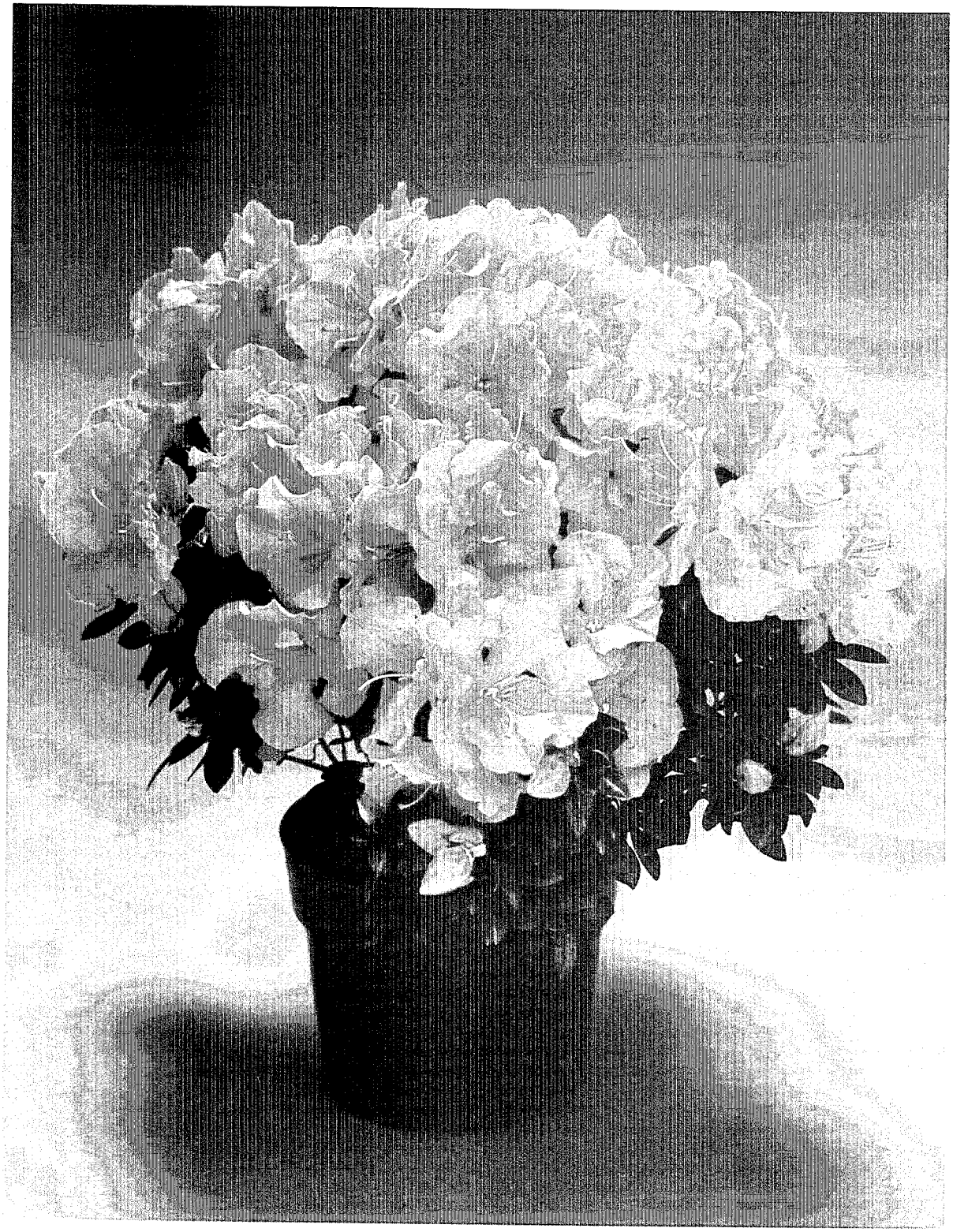

* * * * *